United States Patent
Jones

(10) Patent No.: US 8,416,409 B2
(45) Date of Patent: Apr. 9, 2013

(54) METHOD OF ELLIPSOMETRIC RECONNAISSANCE

(75) Inventor: Michael I. Jones, Azle, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 358 days.

(21) Appl. No.: 12/793,860

(22) Filed: Jun. 4, 2010

(65) Prior Publication Data

US 2011/0299082 A1 Dec. 8, 2011

(51) Int. Cl.
*G01J 4/00* (2006.01)

(52) U.S. Cl.
USPC ........................................ 356/369; 356/141.1

(58) Field of Classification Search .......... 356/600–601, 356/614, 625, 364–369, 141.1, 139.04, 138.07, 356/4.01; 250/461.1, 203.2, 559.22, 559.29; 345/419, 426, 427; 342/45, 357.06; 244/3.16, 244/3.1, 3.11, 3.15
See application file for complete search history.

(56) References Cited

U.S. PATENT DOCUMENTS

| | | | |
|---|---|---|---|
| 4,333,008 A | 6/1982 | Misek | |
| 4,407,465 A * | 10/1983 | Meyerhoff | 244/3.16 |
| 4,497,065 A | 1/1985 | Tisdale | |
| 4,709,580 A * | 12/1987 | Butts et al. | 73/178 R |
| 4,957,368 A * | 9/1990 | Smith | 356/369 |
| 5,176,689 A * | 1/1993 | Hardy et al. | 606/130 |
| 5,212,535 A | 5/1993 | Miyazaki | |
| 5,285,252 A | 2/1994 | Vareille | |
| 5,311,285 A | 5/1994 | Oshige | |
| 5,335,066 A | 8/1994 | Yamada | |
| 5,375,008 A | 12/1994 | Guerreri | |
| 5,414,577 A * | 5/1995 | Arin et al. | 360/256.3 |
| 5,807,387 A * | 9/1998 | Druais | 606/10 |
| 5,936,734 A | 8/1999 | Johs | |
| 5,955,724 A * | 9/1999 | Livingston | 250/203.2 |
| 5,969,372 A * | 10/1999 | Stavely et al. | 250/559.42 |
| 6,187,018 B1 * | 2/2001 | Sanjay-Gopal et al. | 606/130 |
| 6,255,787 B1 * | 7/2001 | Belleveau | 315/312 |
| 6,373,871 B1 | 4/2002 | Hemmes | |
| 6,469,788 B2 | 10/2002 | Boyd | |
| 6,943,880 B2 | 9/2005 | Kanzaki | |
| 6,974,964 B1 * | 12/2005 | Wang | 250/559.29 |
| 6,982,792 B1 | 1/2006 | Woollam | |
| 7,006,222 B2 * | 2/2006 | Krishnan | 356/369 |
| 7,321,427 B2 | 1/2008 | Ebert | |
| 7,359,041 B2 * | 4/2008 | Xie et al. | 356/141.1 |
| 7,420,675 B2 | 9/2008 | Giakos | |
| 7,428,050 B2 | 9/2008 | Giakos | |
| 7,473,884 B2 * | 1/2009 | Fouquet et al. | 250/221 |
| 7,767,945 B2 * | 8/2010 | Williams | 244/3.16 |
| 2001/0015414 A1 * | 8/2001 | Keranen et al. | 250/559.45 |
| 2003/0090669 A1 * | 5/2003 | Jung et al. | 356/450 |
| 2007/0221863 A1 * | 9/2007 | Zipf | 250/461.1 |

* cited by examiner

*Primary Examiner* — Sang Nguyen
(74) *Attorney, Agent, or Firm* — Bracewell & Giuliani LLP

(57) ABSTRACT

A method of obtaining information about a target by using an ellipsometric technique of illuminating the target with coherent light beams from moveable light sources and recording reflections from the target. By analyzing the reflections, the surface material refractive index or dielectric tensors may be classified to yield information about the surface material properties. The beams can be emitted at different polarities and/or different frequencies. Ultra-coherent lasers can be used to produce beams that illuminate targets up to 100 kilometers from the beam source.

20 Claims, 4 Drawing Sheets

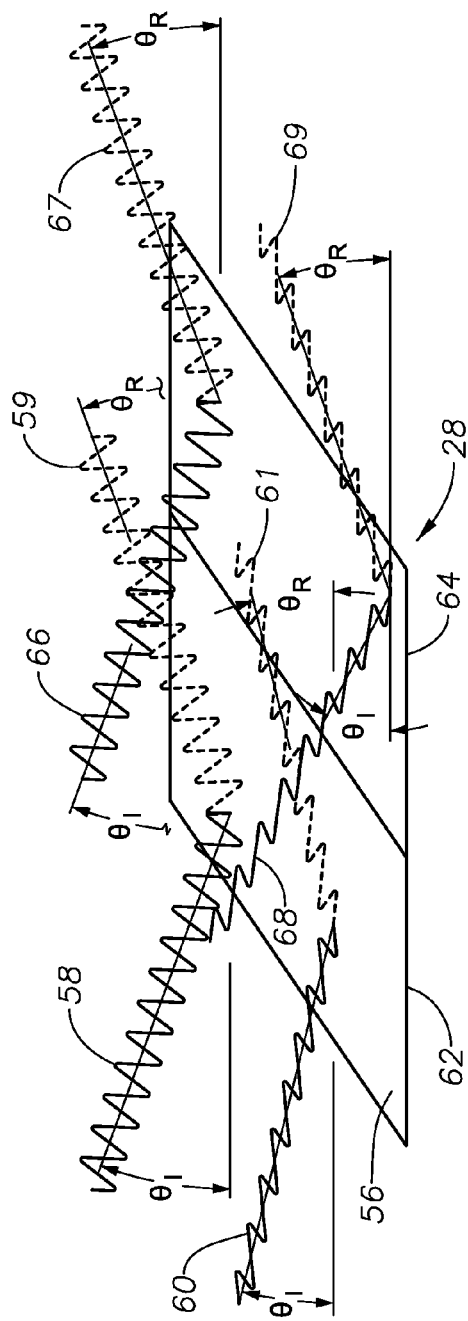
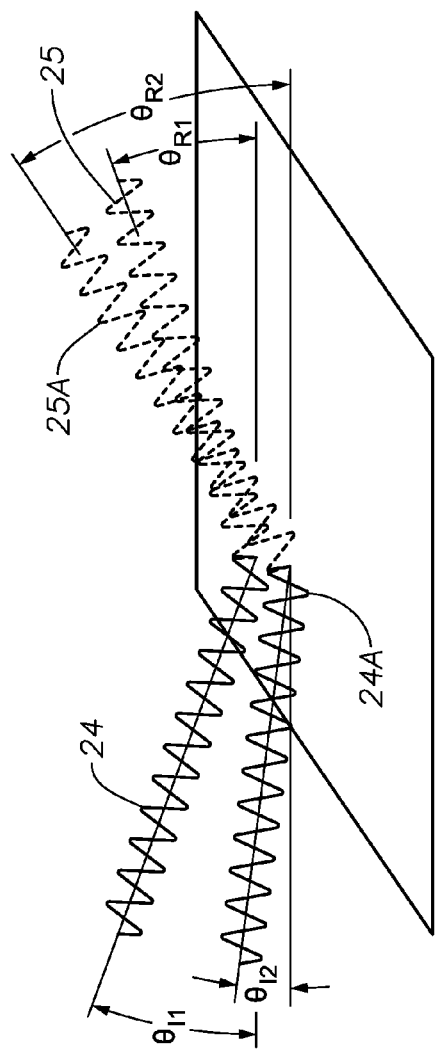
Fig. 4
Fig. 5

METHOD OF ELLIPSOMETRIC RECONNAISSANCE

BACKGROUND

1. Field of Invention

The present disclosure relates generally to a method of characterizing a target using ellipsometry. More specifically, the present disclosure relates to illuminating a target beams of light with more than one moveable objects, recording reflections from the target, and identifying target characteristics based on the recorded reflections. Yet more specifically, the present disclosure relates to illuminating a target with two separately directed beams of linearly polarized light projected from two disparate airborne platforms at orthogonal polarization orientations, recording polarized reflections from the target, and identifying target characteristics based on the recorded reflections and polarization analysis.

2. Description of Prior Art

Reconnaissance, target location, and target identification, are necessities when engaged in combat and other military operations. One aspect of reconnaissance, combat related or not, includes identification and/or monitoring of certain targets. Examples of reconnoitered targets include weapons based vehicles, such as fighter and/or bomber aircraft (fixed wing as well as rotary), tanks, battleships, missiles, and the like. Transport vehicles can also be tracked as targets, such as personnel carriers (armored or not), trucks, jeeps, cargo aircraft, transport aircraft, ships, and the like. The advent of an increasingly mechanized and technology laden battlefield has increased movement on and to the battlefield, thus increasing the requirements for faster, more responsive, and more accurate and discriminating reconnaissance.

Currently, targets can be directly imaged using broadband visible light, short, mid, or long wavelength infrared, as well as near-monochromatic laser light. Hyperspectral sensors can be employed to provide a spectral signature and/or target imagery, with a limited degree of spectral/spatial resolution. The target image may yield its shape, aspect ratio, orientation, range, polarization behavior, and time resolved vibration signatures. Target surface properties of texture and/or color may be assessed using a land based laser radar, but at highly degraded resolution compared to optical systems.

SUMMARY OF INVENTION

Disclosed herein is an example embodiment of a method of ellipsometric reconnaissance that includes providing a first moveable object and a second moveable object. The first and second moveable objects have first and second light sources respectively. The method can further include illuminating a target with light from the first light source and illuminating the target with light from the second light source. In an example, the second light source emits light with an operating parameter that is different from light from the first light beam. Also included with the method are steps of receiving at least a portion of light from the first and second light sources that has reflected from the target and identifying the target surface material based on the received reflected light. The method can further include illuminating the target with the first light source at a different angles of incidence. In an example embodiment, the step of identifying the target surface material based on the received reflected light includes measuring a light parameter change caused by its reflection from the target surface. The light parameters can be polarization, wavelength, frequency, flux, amplitude, as well as phase. Different portions of the target can be illuminated by repeating illumination steps. Example embodiments exist where a laser is used as first and second light sources. Light from the first and second light sources can have a wavelength of from about 100 THz to about 200 THz, from about 125 THz to about 175 THz, or about 150 THz. In an example embodiment, light from the first and second light sources can be coherent up to at least about 100 kilometers. The first and second light sources may optionally be calibrated, in an example embodiment calibration occurs by directing light from the first and second light sources to a surface of a calibration target having a known material. Light can be received reflects from a surface of the calibration target, and then parameters of the received light reflected from the target can be compared with received light reflected from the calibration target. The moveable objects can be aircraft, spacecraft, water craft, land based vehicles, and personnel moveable objects. Optionally, the range of incidence angles formed by the light from the sources contacting the target surface can be maximized. The method can alternatively include identifying different materials on the target surface.

Also disclosed herein is a method of analyzing a target that includes creating first and second reflections from the target by illuminating the target with first and second lights directed respectively from first and second moveable objects. The second light may have an operating parameter offset from the operating parameter of the first light. The first and second reflections can be received, and a material on the target may be identified based on a comparison of the first and second reflections. The light parameter can be polarization, wavelength, frequency, flux, amplitude, or phase. Creating the first and second reflections can be repeated at different angles of incidence between the light and target. The light can be formed using an ultra coherent laser adapted to generate a laser that is coherent up to around 100 kilometers.

Yet further disclosed herein is a method of identifying a target having a surface. In one example embodiment the method includes directing towards the target, first and second light beams that are coherent up to around 100 kilometers and are respectively from first and second moveable objects. The light beams illuminate the target and form first and second reflections. In an example embodiment, the second light beam has an operating parameter different from the first light beam. The reflections can be received and compared to operating parameters of the first and second light beams and used to identify material on the target. The method can be repeated at different angles of incidence. The illumination steps can be repeated to illuminate different portions of the target and then the material on the different portions of the target can be identified.

Disclosed herein is a method of enhancing the positive location and identification of a target by using two separately projected, linearly polarized beams of light originating from two different aircraft flying in a coordinated surveillance pattern. In an example embodiment, the polarization of these two beams can be maintained under electro-optic (EO) modulator control to be orthogonal, in vertical and horizontal orientation, regardless of aircraft orientation and location. The polarization vector from each aircraft can be sequentially alternated from horizontal to vertical, and time-controlled such that the simultaneous target illumination may always be orthogonal. The aircraft, possibly manned or unmanned, can have, via on-board instrumentation, precise real-time knowledge of three-dimensional positions in space relative to each other, individual range to the suspected target, polarization orientation of the emitted beams, and the precise knowledge of the projected angle between the two beams. In an example embodiment, the optical arrangement performs as an ellipsometer and is capable of estimating the complex index of refraction of a material creating the sensed backscattered or reflected energy. The ellipsometer described herein is operable up to several kilometers, unlike a few centimeters such as is typical for a laboratory instrument.

The features and benefits of basic ellipsometric measurements are that materials that have any significant surface interaction with light, whether by refraction, reflection or scattering, that modifies the polarization behavior of the affected light, can be more accurately analyzed and classified using ellipsometric measurements. Refracting materials include window glass, transparent plastics, aircraft canopies and transparencies, missile domes, surface paints and treatments using partially transparent binders, electro-optical windows on internally or externally mounted EO sensors. Purely reflecting materials do not typically alter polarization significantly, but can provide "second-bounce" reflections from light sources that do have strong polarization. Scattering can also modify polarization, including scattering from airborne aerosols and molecules, binders and pigment particles in paints, etc.

Standard ellipsometric data reduction formulas calculate the complex index of refraction of a material under test, provided the angles between the two orthogonally polarized beams are known (from GPS lat/long/altitude differences on the two aircraft), and an estimate of the angle of incidence on the test surface is available. In an example embodiment of the method disclosed herein, multiple backscattered return averaging and reduction of forward motion blurring may be obtained by pulsing the lasers. The polarization may alternate from horizontal to vertical in one beam, and simultaneously from vertical to horizontal in another beam, providing a way to maintain system calibration and enhance data accuracy. Bursts of closely spaced nanosecond to microsecond laser pulses can be emitted from each aircraft and sensed by the other. Differences in horizontal and vertical polarization may be input to the ellipsometric formulas, and the onboard computers can calculate the complex index of refraction from them. A library of complex index of refraction values for many different materials may be searched to find the closest match to the illuminated material. This information, merged with direct imagery of the target and any hyperspectral information available, may be used to increase the probability of identification of the target for appropriate action.

BRIEF DESCRIPTION OF DRAWINGS

Some of the features and benefits of the present invention having been stated, others will become apparent as the description proceeds when taken in conjunction with the accompanying drawings, in which:

FIG. 4 illustrates a perspective schematic of beams illuminating and reflecting from different sections of a target surface.

FIG. 5 is a schematic perspective view of a beam illuminating a target surface at different angles of incidence.

Figure 1:
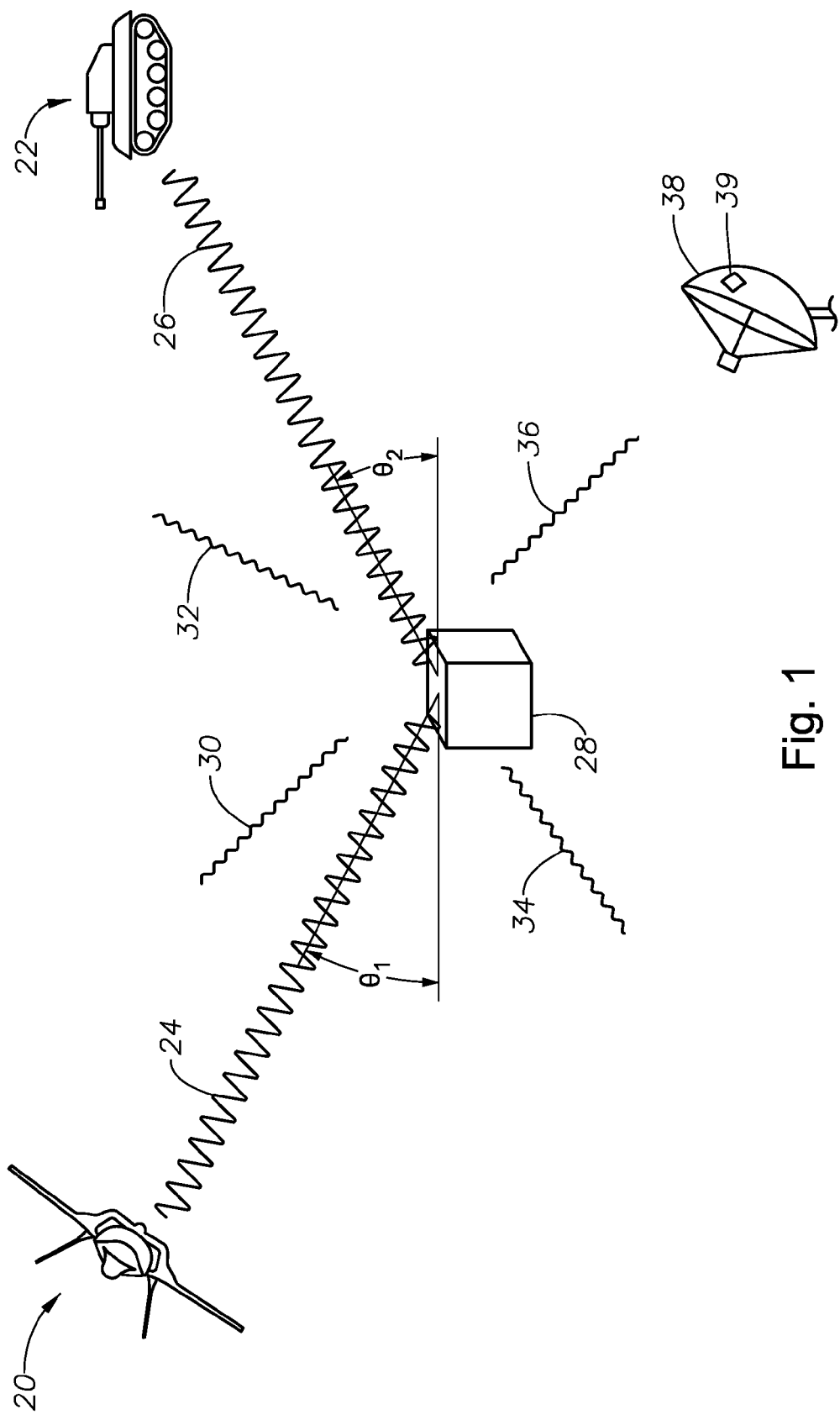
FIG. 1 schematically illustrates in perspective view beams from movable objects illuminating a target.

While the subject matter herein will be described in connection with enabling embodiments and at least a preferred embodiment, it will be understood that applicant's subject matter is not limited to the embodiment(s) provided. On the contrary, the present application is intended to cover all alternatives, modifications, and equivalents, as may be included within the spirit and scope of the applicant's subject matter as defined by the appended claims.

DETAILED DESCRIPTION OF INVENTION

Details of the advantage(s) presented herein will now be described more fully hereinafter with reference to the accompanying drawings in which embodiments are shown. The subject matter of this disclosure may, however, be embodied in many different forms and should not be construed as limited to the illustrated embodiments set forth herein; rather, these embodiments are provided so that this disclosure will be thorough and complete, and will fully convey the scope to those skilled in the art. Like numbers refer to like elements throughout. For the convenience in referring to the accompanying figures, directional terms are used for reference and illustration only. For example, the directional terms such as "upper", "lower", "above", "below", and the like are being used to illustrate a relational location.

It is to be understood that the subject of the present disclosure is not limited to the exact details of construction, operation, exact materials, or embodiments shown and described, as modifications and equivalents will be apparent to one skilled in the art. In the drawings and specification, there have been disclosed illustrative embodiments of the invention and, although specific terms are employed, they are used in a generic and descriptive sense only and not for the purpose of limitation. Accordingly, applicant's right to exclude is therefore to be limited only by the scope of the appended claims.

Disclosed herein is a method of target reconnaissance useful for analyzing a target and obtaining its characteristics. In one example, long range stand-off reconnaissance of a target is performed using beams of electromagnetic energy. In this example, the target is illuminated in accordance with an ellipsometric method; beam reflections from the target can then be collected and analyzed. Methods of ellipsometry include measuring changes in amplitude, phase, and polarization of electromagnetic beams reflected or scattered from the target, or transmitted through the target. From the reflected beams, a complex refractive index or dielectric tensor of target material is quantifiable. It is within the capabilities of those skilled in the art to access known equations to obtain the refractive index in dielectric tensor from this analysis. The ellipsometric method can include illuminating the target surface over a range of incidence angles.

By analyzing the beam reflections, target surface material properties can be identified, including chemical composition and electrical conductivity. This is turn enables classification of target surfaces into metals, glass, plastic, paints, paint compositions, imbedded particulates, and low observable treatments, and the like. Beam analysis includes ascertaining the beam parameters, such as wavelength, polarization, frequency, phase, flux, intensity, and the like.

The beams considered for use with the present method include beams produced by lasers, including ultra-coherent lasers. For purposes of discussion herein, an ultra-coherent laser can produce a beam that is coherent up to at least about 100 kilometers. Employing an ultra-coherent laser enables illumination of the target in amplitude as well as phase, which is an advantage over simply illuminating the target solely with power, such as the case in conventional laser illuminators in rangers. Optionally, the beam produced by the ultra-coherent laser can have an optical frequency ranging from about 100

THz to about 200 THz and all values between. In one example the beam frequency is about 150 THz.

The method disclosed herein can optionally include adaptive optics for improving the received image. As is known, adaptive optics can reduce distortion within the received signal that may be caused by time varying line of sight jitter, waive front errors introduced as the beam propagates within the atmosphere, as well as distortion caused by turbulent flow through which the beam may pass. The adaptive optics can include hardware and/or software and may account for temporal and spatial properties of distortion within the received beam or signal.

Referring now to FIG. 1 an example of using an ellipsometric technique for analyzing a target is illustrated in a side perspective schematical view. In this example, movable objects 20, 22 are shown emitting beams 24, 26 that illuminate a target 28. Movable object 20 is illustrated as a fixed wing aircraft and includes a beam source (not shown) for producing the corresponding beam 24. As noted above, the beam 24 can be an electromagnetic beam that can include the full spectrum of light, as well as laser beams, ultra-coherent laser beams, and radio beams. Optionally, as illustrated by movable object 22, the movable objects can be land based vehicles. Alternative embodiments include the movable objects 20, 22 both being aircraft, either fixed wing or rotary, or both land based. They can be manned or unmanned and can further include any type of watercraft as well as spacecraft. Yet further alternative embodiments include non-mechanized movable objects that are portable and manually transported to different locations. It should be pointed out, that the number of movable objects is not limited to two but can include more than two or a single movable object for illuminating a target.

Beam 24 is shown contacting a surface of the target 28 at an angle of incidence $\theta_1$. Beam 26 is shown contacting a surface of the target 28 at incidence angle $\theta_2$, wherein $\theta_1$ and $\theta_2$ can be the same or different values. Although the surface on the target 28 is shown as substantially planar, incidences may occur where a target surface is non-planar so that a reflected beam's angle of incidence with the surface is different from the illuminating beam's angle of incidence. Thus, example reflected beams 30, 32, 34, 36 are illustrated that represent reflections of the illuminating beams 24, 26. The reflected beams 30, 32, 34, 36 can be received with a receiver 38, optionally the movable objects 20, 22 may include receivers for receiving these beams. Further schematically illustrated on receiver 38 is an adaptive optics module 39 for correcting any distortion in a received reflected beam.

Figure 2:
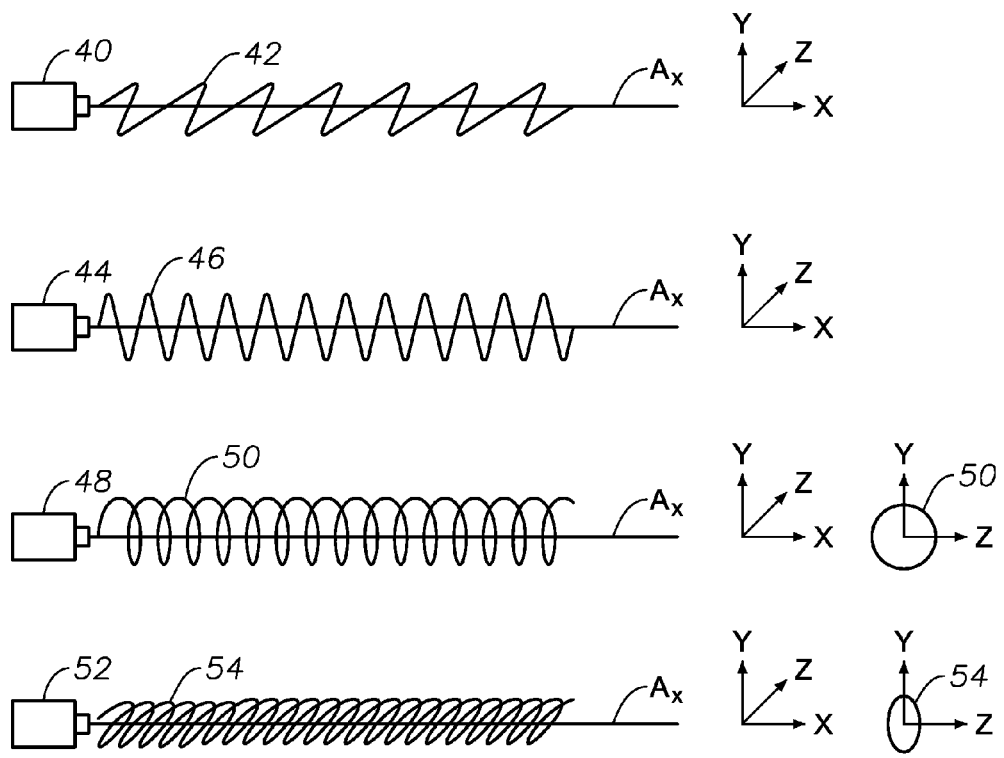
FIG. 2 depicts a side view of example light sources and corresponding beams.

Referring to FIG. 2, illuminating beams having different polarizations are shown in side view with their corresponding sources. A horizontally polarized beam 42 is shown propagating along an axis $A_x$ from its beam source 40. An example coordinate system is shown adjacent the axis $A_x$ representing X, Y and Z coordinate directions. In this example, the horizontally polarized beam 42 propagates in the X direction and is polarized in the Z direction. A vertically polarized beam 46 is shown produced by its corresponding beam source 44. The vertically polarized beam 46 propagates in the X direction and is polarized along the Y axis. Beams for use in the method disclosed herein can include the horizontally and vertically polarized beams 42, 46 as well as beams polarized in different linear orientations; such as beams polarized in a plane oblique to both the Y and Z axis.

Alternatively, non-linearly polarized beams may be used with the method herein. A circularly polarized beam 50 is an example of a non-linearly polarized beam, circularly polarized beam 50 is shown produced by beam source 48 and propagating along the axis $A_x$. An axially view of the circular polarized beam 50 is shown illustrating it is polarized in the Y and Z axis. In another alternative, an illuminating beam in accordance with this disclosure can be an elliptical beam 54 as shown emanating from beam source 52 and propagating along axis $A_x$. Also provided in an axial view, the elliptical beam 54 has a major axis oriented with the Y axis. However other embodiments exist wherein the major axis can be any angle about the X axis.

Figure 3:
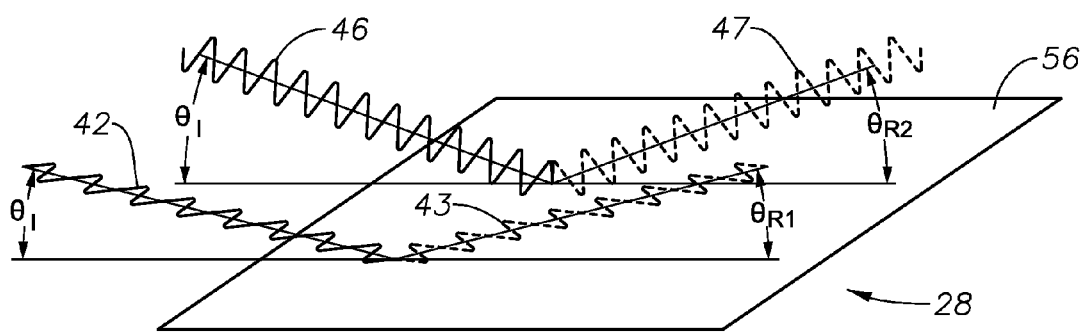
FIG. 3 schematically represents a perspective view of beams illuminating and reflecting from a target surface.

Schematically depicted in a perspective view FIG. 3, is an example of ellipsometric analysis of a target using differently polarized illumination beams. More specifically, a horizontally polarized beam 42 is shown contacting it surface 56 of the target 28 at an incidence angle $\theta_I$. Beam 42 reflects from the surface 56 to form a reflected beam 43 shown reflecting at an incidence angle $\theta_R$. A substantial, portion of the horizontally polarized beam 42 reflects from the surface 56 so that its reflected beam 43 has substantially the same energy as the horizontally polarized illumination beam 42. A vertically polarized beam 46 is also shown contacting the surface 56. The vertically polarized beam 46 contacts the surface 56 at an incidence angle $\theta_I$. The angles of incidence between the horizontal and vertical beams 42, 46 may be the same or different. The corresponding reflection beam 47 is shown reflecting from the surface 56 at reflection angle $\theta_R$. A portion of the vertically polarized beam 46 penetrates the target surface 56. Accordingly, the power of the vertically polarized reflection beam 47 is less than the vertically polarized illumination beam 46. This change in power is reflected in the figure by the dashed representation of the reflected beam 47.

The target surface 56 material affects the respective angles of incidence of the reflected beams 43, 47. Additionally, the phase, polarity, frequency, and intensity of the beams 43, 47 can also be affected or influenced by the material on the target surface 56. Accordingly, target surface 56 material may be identified based on an analysis of the properties/parameters of the reflection beams 43, 47. Also useful, is a comparison of any parameter changes between the illumination beams 42, 46 and their respective reflection beams 43, 47 occurring during illumination beam reflection.

Optionally, the target surface may be partitioned into different portions, and those individual portions each illuminated and analyzed. An example of this is schematically illustrated in perspective view in FIG. 4. In this example, a first illumination beam 58 contacts a target surface 56 in a first section 62 at an angle of incidence $\theta_I$. A first reflected beam 59 reflects from the surface 56 at an angle $\theta_R$. A second illumination beam 60 also strikes the first section 62 at an angle of incidence $\theta_1$, where its angle of incidence $\theta_1$ may be the same or different from the first illumination beams angle of incidence $\theta_I$. A corresponding second reflection beam 61 is shown reflecting at its angle of incidence $\theta_R$, which may be the same or different from the reflected angle of incidence $\theta_R$ of the first reflection beam. The first illumination beam 58 is shown as a vertically polarized beam and the second illumination beam 60 is shown as a horizontally polarized beam. However, the illumination beams can be polarized in any fashion, including the types of beam polarization described above. Moreover, it should be pointed out that the illumination beams may also differ in wavelength, frequency, intensity as well as other parameters.

Adjacent the first section 62 is a second section 64 shown illuminated by a third illumination beam 66 at an angle of incidence $\theta_I$. A third reflection beam 67 reflects from the target surface 56 at an angle $\theta_R$. As noted above, analysis of the reflected beams can yield information about the target including the surface material. Thus by partitioning and analyzing sectors of the target a more comprehensive identification of the target itself is available. Also contacting the second section is a fourth illumination beam 68 contacting the target surface 56 at incidence angle $\theta_1$ and producing a corresponding reflection beam 69 with angle of incidence $\theta_R$. In one example, the third and fourth illumination beams 66, 68 are from the same beam source as one or both the first and second illumination beams 58, 60. In this instance the beam sources are redirected by a beam source operator to illuminate the second section 64. Optionally however the third and fourth illumination beams 66, 68 may come from a beam source different from the source of the first or second illumination beams 58, 60.

Referring now to FIG. 5, an alternative method of ellipsometric target identification is provided in a side perspective view. In this example an illumination beam 24 is shown illuminating a target 28 on its surface 56. The beam 24 contacts the surface 56 at incidence angle $\theta_{I1}$ and reflects at incidence angle $\theta_{R1}$ forming reflection beam 25. Another illumination beam 24A is directed at the target 28 contacting the surface 56 at an angle of incidence $\theta_{I2}$ that is different from $\theta_{I1}$. This produces a corresponding reflection beam 25A shown reflecting at incidence angle $\theta_{R1}$. Employing movable objects as a platform for the sources of the illuminating beams provides an advantage of the ability to change locations so that the target surface 56 can be illuminated with illumination beams at more than one angle of incidence. This is useful in target identification because the corresponding angle of incidence $\theta_R$ for the reflection beam, as well as reflection beam parameters, can vary with the angle of incidence $\theta_1$ of the illumination beam or beams. This further enhances identification of the material or materials on the target surface 56. For example, directing an illumination beam at a particular angle of incidence with the target surface could result in a reflection beam having similar or indistinguishable parameters and/or angle of incidence for two different materials. However, by illuminating the target surface 56 at multiple angles of incidence maximizes the chances the resulting reflective beams will have parameters and angles of incidence unique to that material.

Alternatively, a mission plan for the movable objects 20, 22 can be created prior to their steps of illuminating a particular target. A mission plan criteria can include a path or trajectory that optimizes a maximum range of mono-static as well as bi-static incidence angles of the beams illuminating the target. Optionally, the incidence angles can be within a particular range that is less than the maximum range of incidence angles. Optimizing the ranges of mono-static and/or bi-static incidence angles can improve accuracy and precision of the ellipsometric data further enhancing certainty values assigned to the classification and discrimination of target materials.

Figure 6:
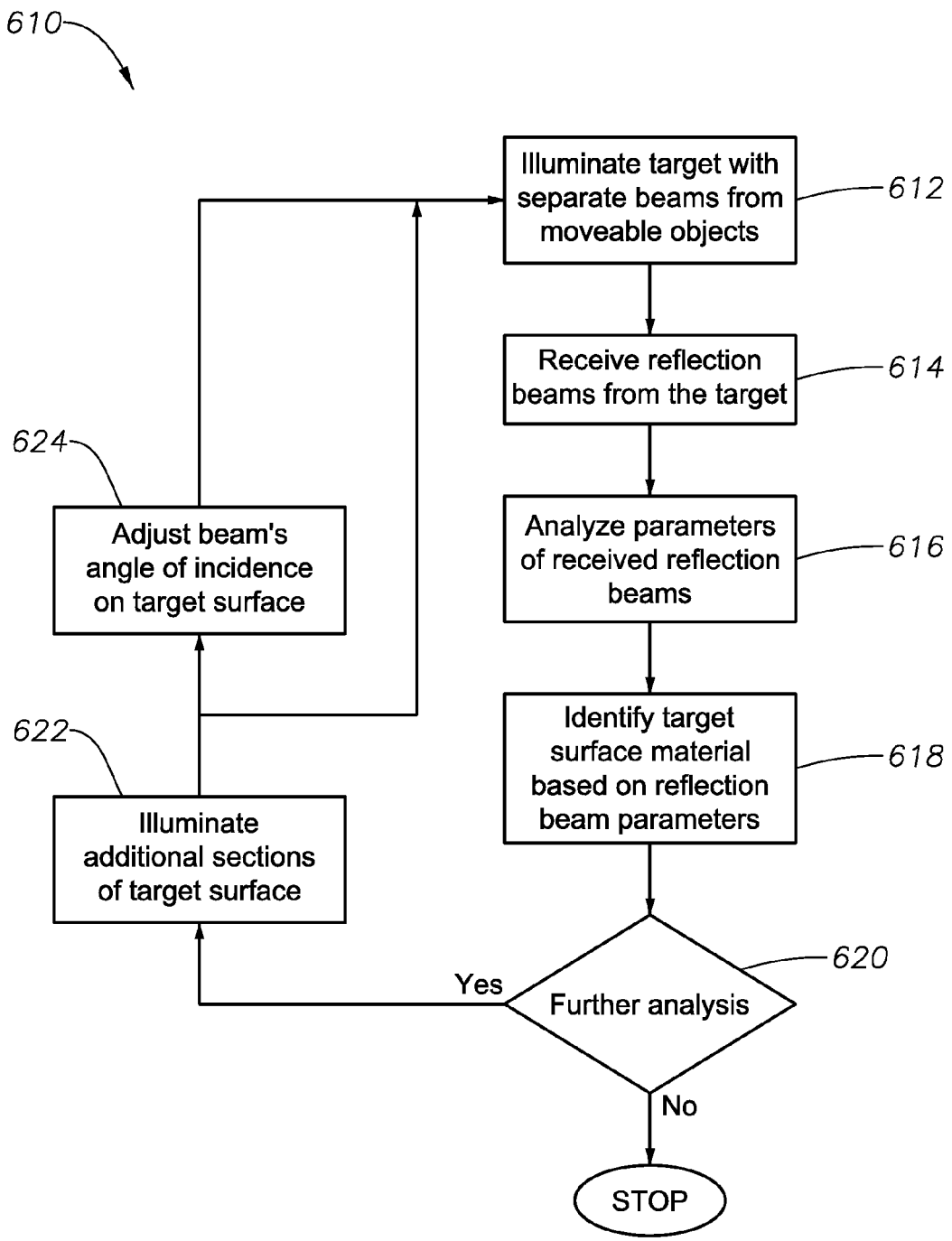
FIG. 6 is a schematic having a flowchart with steps of an example method of ellipsometric reconnaissance in accordance with the present invention.

One example of the present method is illustrated in a flowchart in FIG. 6. Flowchart 610 includes illuminating a target with separate beams from movable objects. Beams may emanate from beam sources on separate movable objects or on different portions of the same movable object (step 612). The beams may include those listed above among others. The illumination beams reflect from the target surface and form reflection beams that are then received using a receiver (step 614). The receivers can be optical members adapted to receive and record light such as full spectrum light and/or laser beams, including ultra-coherent laser beams. The receivers can be associated with or connected onto the movable objects, or optionally can be ground based. In an alternative, the receivers may be associated with or on movable objects that do not have the illumination beams. Since target material can have an effect on the reflection beam parameters, analyzing the reflection beam parameters can provide an indication of the target material. More specifically analyzing the received beams can identify materials on the target surface (step 616). The beam parameters may include polarization, wavelength, frequency and reflective angle of incidence. These parameters can be compared with the illumination beam parameters to obtain differences between the respective illumination and reflective beams parameters; thus information regarding the target surface may be assessed (step 618). An additional parameter is beam intensity and well as beam flux.

Further analysis (step 620) can optionally be performed that includes illuminating additional sections of the target surface (step 622). Since targets can include different materials, i.e. glass, composites, coatings, elastomers, sectoring the target into portions and analyzing those specific portions can identify different target materials. Compiling a list of the different materials can aid in indicating the type and/or size of the target. Optionally, the illumination beam angle of incidence on the target surface may be adjusted (step 624) with additional illumination sequences. This step may occur in conjunction with illumination of multiple portions of the target and can be limited to a single illumination beam or each of the illumination beams. The step of adjusting the angle of incidence can occur by moving the movable object on which the beam source is attached. Optionally, a gimbaling mechanism can be included with the beam source, and the source moved or pivoted around an axis with respect to the movable object on which it is associated.

It should be pointed out that in each of these steps of illumination when multiple beams are used, the beams can have at least one parameter different from the other beam or beams. In one example of use, a first and second illumination beam are used for irradiating a target wherein the first and second beams have different frequencies. This provides a signature to the beam, so when the reflected beam corresponding to that illumination beam is received, the reflection beam may be correlated to the illumination beam based on its frequency. Optionally, other parameters can be used for assessing a signature to a particular illumination beam.

The subject matter described herein, therefore, is well adapted to carry out the objects and attain the ends and advantages mentioned, as well as others inherent therein. While a presently preferred embodiment of the subject matter has been given for purposes of disclosure, numerous changes exist in the details of procedures for accomplishing the desired results. These and other similar modifications will readily suggest themselves to those skilled in the art, and are intended to be encompassed within the spirit of the advantage(s) disclosed herein and the scope of the appended claims.

What is claimed is:

1. A method of ellipsometric reconnaissance comprising:
   a. providing a first moveable object having a first light source and a second moveable object having a second light source
   b. illuminating a target with light from the first light source;
   c. illuminating the target with light from the second light source having at least one operating parameter different from light from the first light beam;
   d. receiving at least a portion of light from the first and second light sources that has reflected from the target; and
   e. using a computer to identify the target surface material based on the received reflected light.

2. The method of claim 1, further comprising illuminating the target with the first light source at an angle of incidence different from that of step (b).

3. The method of claim 1, further comprising illuminating the target with the second light source at an angle of incidence different from that of step (c).

4. The method of claim 1, wherein step (e) comprises measuring a light parameter change caused by reflection of the light from the target surface.

5. The method of claim 1, wherein the light parameters of step (c) are selected from the list consisting of polarization, wavelength, frequency, flux, amplitude, and phase.

6. The method of claim 1, further comprising repeating steps (b) and (c) so that different portions of the target are illuminated.

7. The method of claim 1, wherein the first and second light sources each comprise a laser.

8. The method of claim 1, wherein the light from the first and second light sources has a wavelength selected from the list consisting of from about 100 THz to about 200 THz, from about 125 THz to about 175 THz, and about 150 THz.

9. The method of claim 1, wherein the light from the first and second light sources is coherent up to at least about 100 kilometers.

10. The method of claim 1, further comprising calibrating the first and second light sources by directing light from the first and second light sources to a surface of a calibration target having a known material, receiving light reflecting from the surface of the calibration target, and comparing parameters of the received light reflected from the target with received light reflected from the calibration target.

11. The method of claim 1, wherein the moveable cable objects are selected from the list consisting of aircraft, spacecraft, water craft, land based vehicles, and personnel moveable objects.

12. The method of claim 1, further comprising, maximizing range of incidence angles formed by the light from the sources contacting the target surface.

13. The method of claim 1, further comprising identifying different materials on the target surface.

14. A method of analyzing a target comprising:
   a. creating a first reflection from the target by illuminating the target with a first light from a first moveable object;
   b. creating a second reflection from the target by illuminating the target with a second light from a second. moveable object, the second light having an operating parameter offset from the operating parameter of the first light;
   c. receiving the first and second reflections; and
   d. using adaptive optics to correct distortion in one of the reflections;
   e. comparing the first and second reflections in a computer to identify a material on a portion of the target proximate where the first and second lights illuminate the target.

15. The method of claim 14. wherein the light parameter of step (b) is selected from the list consisting of polarization, wavelength, frequency, flux, amplitude, and phase.

16. The method of claim 14, further comprising repeating steps (a) and (b) at a different angle of incidence between the light and target.

17. The method of claim 14, further comprising forming the light using an ultra coherent laser adapted to generate a laser that is coherent up to around 100 kilometers.

18. A method of identifying a target having a surface, the method comprising:
   a. directing at the target from a first moveable object, a first light beam that is coherent up to around 100 kilometers that illuminates the target and forms a first reflection;
   b. directing at the target from a second moveable object, a second light beam that illuminates the target and forms a second reflection, the second light beam having an operating parameter different from the first light beam;
   c. receiving the reflections;
   d. comparing the operating parameters of the first and second light beams respectively to the first and second reflections; and
   e. using a computer to identify material on the target based on the results of step (d).

19. The method of claim 18, further comprising repeating steps (a) and (b) at different angles of incidence.

20. The method of claim 18, further comprising repeating steps (a) and (b), wherein the repeated steps (a) and (b) include illuminating different portions of the target and repeating step (e), wherein repeated step (e) includes identifying material on the different portions of the target.

* * * * *